(12) United States Patent
Fan et al.

(10) Patent No.: US 8,197,408 B2
(45) Date of Patent: Jun. 12, 2012

(54) SPARSE TISSUE PROPERTY MEASUREMENTS IN MEDICAL ULTRASOUND IMAGING

(75) Inventors: Liexiang Fan, Sammamish, WA (US); Paul Freiburger, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1060 days.

(21) Appl. No.: 12/038,683

(22) Filed: Feb. 27, 2008

(65) Prior Publication Data
US 2009/0216119 A1    Aug. 27, 2009

(51) Int. Cl.
*A61B 8/00* (2006.01)
(52) U.S. Cl. ........................................ 600/438
(58) Field of Classification Search .................. 600/438
See application file for complete search history.

(56) References Cited

U.S. PATENT DOCUMENTS

| | | | |
|---|---|---|---|
| 5,107,837 A | 4/1992 | Ophir et al. | |
| 5,178,147 A | 1/1993 | Ophir et al. | |
| 5,293,870 A | 3/1994 | Ophir et al. | |
| 5,810,731 A | 9/1998 | Sarvazyan et al. | |
| 6,508,768 B1 | 1/2003 | Hall et al. | |
| 6,558,324 B1 | 5/2003 | Von Behren et al. | |
| 6,770,033 B1 | 8/2004 | Fink et al. | |
| 6,951,544 B2 | 10/2005 | Trahey et al. | |
| 7,871,380 B2 * | 1/2011 | Waki et al. | 600/443 |
| 2005/0004463 A1 | 1/2005 | Chen et al. | |
| 2005/0252295 A1 | 11/2005 | Fink et al. | |
| 2006/0173319 A1 * | 8/2006 | Sumi | 600/437 |
| 2007/0238966 A1 * | 10/2007 | Sun et al. | 600/407 |
| 2010/0222678 A1 * | 9/2010 | Bercoff et al. | 600/442 |

FOREIGN PATENT DOCUMENTS
WO    WO2006/022238    *    3/2006

OTHER PUBLICATIONS
U.S. Appl. No. 11/824,388, filed Jun. 28, 2007.

* cited by examiner

*Primary Examiner* — Jacqueline Cheng

(57) ABSTRACT

The shear modulus information is measured for sparse locations in a scanning field of view. For other locations, the shear modulus information is calculated as a function of the sparsely measured values and strain information. For example, shear modulus values are provided for every grid point in a field of view based on strain values for every grid point and on sparsely measured shear modulus values.

17 Claims, 2 Drawing Sheets

SPARSE TISSUE PROPERTY MEASUREMENTS IN MEDICAL ULTRASOUND IMAGING

BACKGROUND

The present embodiments relate to tissue property ultrasound imaging. Tissue is a viscoelastic material. Strain, shear, hardness, stiffness, or other property of tissue may be determined.

One tissue property or component of viscoelasticity is elasticity. Ultrasound imaging may operate in an elasticity imaging mode. U.S. Pat. Nos. 5,107,837; 5,293,870; 5,178,147; and 6,508,768 describe methods to generate elasticity images using the relative tissue displacement between adjacent frames. The tissue strain is determined in response to a stress applied to tissue. The stress is applied externally, such as by manual pressure or by acoustic pressure. Strain or strain rate are detected for generating an elasticity image. Shear velocity and relaxation time of tissue under stress may be determined. Altered stiffness regions may be identified. However, strain is relative or qualitative. For example, different amounts of applied stress result in different amounts of strain. The amount of applied stress may be unknown or difficult to accurately determine.

Pressure sensors may be used to determine the amount of manually applied pressure at the surface of the skin. However, pressure sensors may not be available or accurate for determining internal stress. Acoustic radiation force may be transmitted at a known amplitude. However, aberrations or other propagation errors may limit accuracy of determined stress applied at the internal tissue. Acoustic force information may not be available, or the amount of acoustic radiation applied to a patient may be limited.

Other parameters may be determined or estimated, such as modulus (e.g., hardness). Modulus may be quantitative, but may require additional transmissions or measurements. Such additional measurements may undesirably delay imaging.

BRIEF SUMMARY

By way of introduction, the preferred embodiments described below include methods, instructions, and systems for determining shear information, viscoelastic tissue property, and/or modulus information. The tissue property (e.g., shear or modulus) information is measured for sparse locations in the scanning field of view. For other locations, the tissue property information is calculated as a function of the sparsely measured values and strain information. For example, shear modulus values are provided for every grid point in a field of view based on strain values for every grid point and on sparsely measured shear modulus values.

In a first aspect, a method is provided for determining shear information with ultrasound. First shear information is estimated at sparse locations of a grid. Second shear information is calculated for a denser sampling of the grid. The calculating of the second shear information is a function of the first shear information. An image is displayed as a function of the second shear information.

In a second aspect, a computer readable storage medium has stored therein data representing instructions executable by a programmed processor for determining modulus information with ultrasound. The storage medium includes instructions for estimating, with ultrasound response, tissue moduli at sparse locations in a field of view, and determining, as a function of the tissue moduli at the sparse locations, tissue moduli at dense locations in the field of view.

In a third aspect, a system is provided for determining viscoelastic tissue property. A transducer is operable to generate receive signals from received ultrasound energy. A receive beamformer is operable to output data representing spatial locations along at least a line. An image processor is operable to apply modulus estimation to a limited number of locations within a field of view, generate strain information as a function of the output data, the strain information being for a greater number of locations within the field of view, and determine viscoelastic tissue property values for the greater number of locations within the field of view as a function of the strain information and the moduli estimated for the limited number of locations.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

By applying external or remote force to tissue, a corresponding displacement or strain image can be generated. However, strain or displacement varies with the amplitude of the applied force or stress. The applied force may be unknown, such as from manual application of pressure or due to unknown propagation path irregularities.

Shear modulus is estimated by inducing shear waves in the field of view. The shear waves are measured with ultrasound, such as by transmitting and receiving along a group of scan lines to measure shear for one location. The shear modulus is calculated from the measured shear wave velocity. The estimated shear modulus is a quantitative value. However, acquiring shear modulus estimates over many locations requires long data acquisition or exposures to high doses of acoustic energy.

The strain or displacement is more rapidly acquired for the many locations in the same field of view. The secondary shear modulus values are calculated from densely sampled strain values and the more sparsely estimated shear modulus values. Other modulus, shear, or tissue property information may be calculated, such as calculating Young's modulus information. The quantitative shear or modulus information or expanded tissue property information may be displayed over the entire field of view with less patient exposure to acoustic energy and possibly less heating of the transducer.

Figure 1:
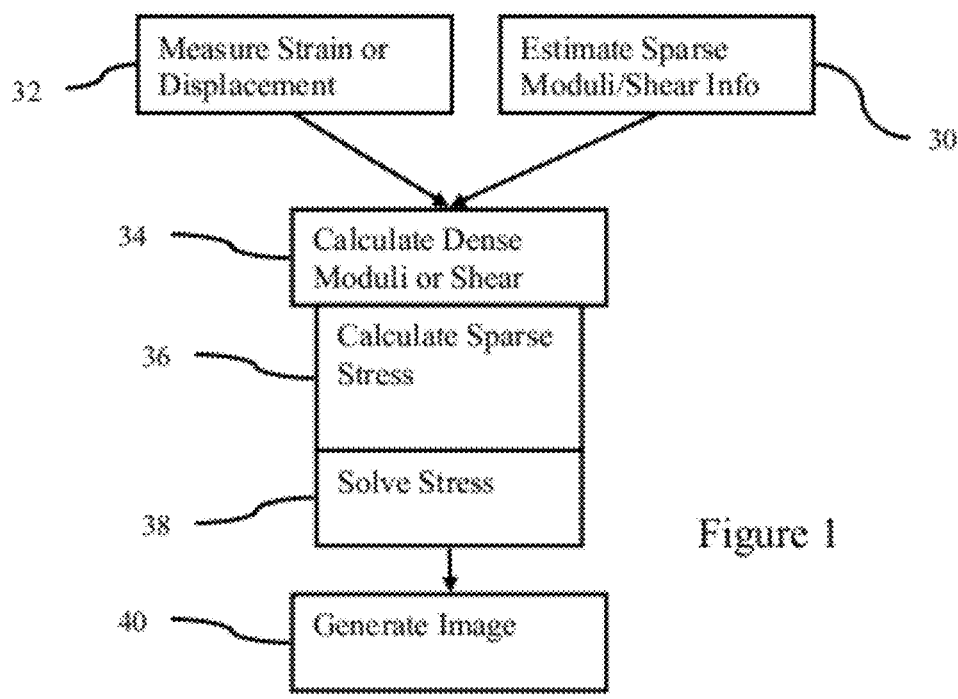
FIG. 1 is a flow chart diagram of one embodiment of a method for determining tissue property with ultrasound.

FIG. 1 shows a method for determining shear or tissue property information with ultrasound. The method is implemented by the system of FIG. 2 or a different system. Additional, different, or fewer acts may be provided. For example, acts 32 and/or 40 are not provided in some embodiments. The acts are performed in the order described or shown, but may be performed in other orders. For example, strain is measured in act 32 before the shear modulus of act 30. FIG. 1 is generally described below for moduli or shear information, but other viscoelastic tissue properties may be used in other embodiments.

In act 30, sparse moduli or shear information is estimated. The scan format and settings determine the field of view. The field of view may be expanded beyond a region for which a transducer is capable of scanning, such as by expanded field of view two-dimensional imaging or by three-dimensional scanning. The scan format provides a plurality of scan lines, such as parallel scan lines in a linear format or diverging scan lines in a sector or Vector® format. Each scan line may be sampled any number of times. The scan line sampling rate and scan line density or distribution provide a grid. Alternatively, a plane wave transmission and Fourier transform based reception provide samples in any desired grid.

Figure 3:
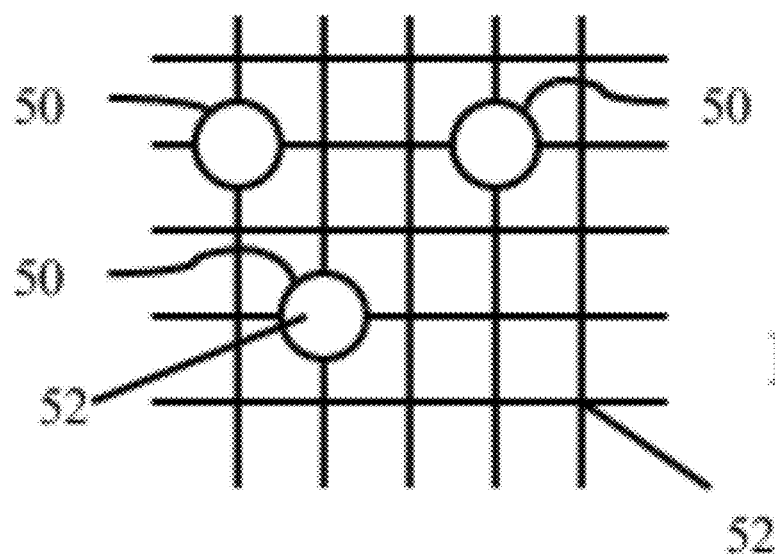
FIG. 3 is a graphical representation of a grid for a field of view with sparse sampling of the grid points.

FIG. 3 shows an example grid. In alternative embodiments, the grid is warped, one or more lines are curved, and/or the border has a different shape. The lines represent scan lines and/or mere representation of a layout of points. The grid includes grid points 52. The grid points 52 represent locations where data may be acquired in a given scan format, such as sample locations along scan lines. Twenty-five grid points 52 are shown for graphic illustration herein, but more or fewer grid points 52 may be provided.

The moduli or shear information is sampled more sparsely than the available grid points 52. For example, FIG. 3 shows three grid points 50 sampled from a possible twenty-five. The moduli or shear information is measured or estimated for these sparse locations representing fewer than all of the possible locations or fewer than all of the locations for which strain is sampled in act 32. The grid points 50 used for sparse sampling may have any density and/or distribution. In one embodiment, the sparse sampling occurs at regularly spaced intervals, such as every five, ten, twenty, or more grid points 52 both laterally and axially.

Any modulus or shear value may be estimated. Tissue modulus values represent the hardness or stiffness at the locations. For example, the shear modulus of tissue is estimated. In alternative embodiments, Young's modulus is estimated. In other embodiments, other shear values are estimated, whether quantitative or qualitative.

Estimation at the sparse locations 50 is provided by direct or indirect measurement. For example, shear modulus values for the sparse locations are estimated from ultrasound response. Ultrasound or other stress is applied to generate a shear wave at the sparse location 50. For example, acoustic radiation force impulse is transmitted with a focal point at or adjacent to the sparse location 50. Other sources of stress may be used, such as manually or internally generated stress. In response to the stress, a shear wave is generated. A plurality of locations around or at the sparse location 50 is scanned with ultrasound. Doppler or B-mode scanning may be used. In one embodiment, the shear wave perpendicular to the direction of the applied stress is detected by obtaining multiple B-mode scans of a small region (e.g., 4 mm in lateral and 5 mm in axial) around, adjacent to, or including the sparse location 50. By correlating the data from the different B-mode scans, the amplitude, velocity, or other characteristic of the shear wave is measured.

The shear modulus is given by $g = \rho v_s^2$, where $\rho$ is density, and v is estimated shear velocity. Other modulus or shear values may be calculated for the sparse locations 50.

In act 32, the strain or displacement is measured. The measurements are for a denser distribution of grid points 52 than the sparse estimation of act 30. Strain or displacement is measured at more of the grid points 52 than for the sparsely sampled moduli or shear information measurements. For example, strain or displacement is determined for a full distribution of the grid or sample points 52. All of the grid points 52 in a region of interest or the entire field of view are used for measuring. In alternative embodiments, strain or displacement is measured at fewer than all of the grid points 52, but at more grid points 52 than the sparse locations 50.

The tissue is strained in response to applied stress. Compression force, rarefaction force, or other stress is applied to tissue being scanned. For example, a user applies pressure axially with a transducer. Ultrasound scanning is performed while applying pressure with the transducer against the patient. Alternatively, another source of stress or compression is used, such as acoustic energy or a mechanical structure.

The stress may be applied by an external source. External pressure includes acoustic or mechanical pressure. The pressure propagates from outside the patient, such as from a transducer probe, to the tissue or region of interest. The pressure may be generated from within a patient, such as acoustic pressure generated from an intra cavity probe. Acoustic pressure may be a focused or unfocused acoustic radiation force. Mechanical pressure may include a machine (e.g., thumper or vibrator).

The applied stress in the tissue may be unknown. For example, manual application of stress is provided without pressure sensors. As another example, the pressure at one location (e.g., skin surface) is known or may be measured, but the resulting pressure at other grid points 52 may be unknown. In yet another example, strain data from a previous scan is loaded into a memory, but without any stress information.

In other embodiments, the applied stress may be determined. For example, a pressure applied manually is measured. As another example, a force applied mechanically or acoustically is measured. In another example, pressure from a source within a patient is estimated. For example, the heart generates pressure within the circulatory system. The pressure within a vessel may be estimated from the velocity profile across the vessel or a velocity at a center of the vessel. Doppler or flow imaging is used to estimate the velocity. The velocity is related to pressure by an empirical or known relationship. The velocity-pressure relationship may be calibrated to an individual patient by measuring static pressure for the patient. As another example, the diaphragm or lungs apply pressure to surrounding tissue during the breathing cycle. The velocity of the tissue is determined by tissue Doppler imaging or tissue tracking. Empirical data or another relationship between the velocity of the diaphragm tissue and pressure is used to estimate the stress. One method to estimate the stress is to measure the pressure at the body surface with sensors attached to the transducer.

The applied stress may be impulse, cyclical, repeating, or a non-impulse stress. For example, the pressure applied due to breathing or the heart is cyclical. The stress is applied repetitively, or differently as a function of time. The applied stress may be represented by an impulse. A substantially single pressure wave is generated. The impulse may be generated by a cyclical pulsed waveform of any number of cycles (e.g., tens or hundreds of cycles). For example, acoustic radiation force is transmitted as an impulse for applying stress to tissue. The impulse wavefront propagates to the region of interest.

Ultrasound imaging is performed before, during and/or after the stress is applied. Ultrasound data is received in response to transmissions of ultrasound. The transmissions and receptions are performed for a single spatial location (e.g., the focal point of the applied stress), along a line, over an area, or over a volume. A sequence of transmissions and receptions are provided for each spatial location.

The displacement of tissue is determined as a function of time. The displacement may be measured from tissue data, such as B-mode ultrasound data. Correlation, cross-correlation, minimum sum of absolute differences or other similarity measure is used to determine the displacement between scans. The displacements are determined along one, two, or three dimensions. In one embodiment, any one or more of the methods or systems disclosed in U.S. Pat. No. 5,107,837; 5,293,870; 5,178,147; 6,508,768 or 6,558,324, the disclosures of which are incorporated herein by reference, are used to generate elasticity frames of data or images as the strain information. Other methods of measuring strain with or without determining displacement of tissue in response to application or change in stress may be used. The displacement may be measured by determining tissue velocity and/or acceleration.

Based on one (e.g., velocity), two (B-mode correlation), or more (e.g., average displacement) scans, a strain field is determined. The strain field represents strain at the different locations. A displacement field or a strain rate field may be used in other embodiments. Other measurements may be used to represent strain or displacement, such as velocity.

The strain or displacement may be determined at different times. A strain or displacement field is calculated from different sets of data. For example, different ultrasound scans are provided for measuring strain at different times separated by milliseconds, seconds, minutes, or longer. The different strain or displacement may be determined from unique sets of data or one or more frames of data may be used for both fields. For example, three scans are performed during a change in stress. A first strain field is calculated from the data of the first two scans, and the second strain field is calculated from the data of the last two scans. The strain at different times is responsive to different applied stresses due to the change in stress. In other embodiments, a different stress, such as different amplitude of stress, is applied in unique or separate stress events, and strain is measured from unique data sets acquired for the separate stress events.

The measured strain is or is not corrected for depth dependent attenuation of the applied stress. As pressure propagates through tissue, the pressure attenuates. Less motion or displacement is caused at locations spaced further from the source of pressure (depth relative to the source) due to the attenuation. The displacement is adjusted to account for the attenuation, providing more normalized displacements or strain at different spatial locations.

The correction is linear as a function of distance away from the point or region of the source of stress. Non-linear correction may be used, such as based on tissue models or different types of tissue. The linear or non-linear function is assumed, based on empirical data, or is based on a propagation model. For acoustic force, the attenuation of sound in tissue as a function of distance and frequency is corrected. For other external force or force from other organs, such as manually applied force or heart force, no or different correction is provided.

The correction is performed in the time domain. In alternative embodiments, the correction is performed in the Fourier or frequency domain.

In act 34, shear or modulus information is calculated for a denser sampling of the grid. For example, shear modulus values for the fully sampled grid are calculated as a function of the shear information at the sparse locations. As another example, the tissue moduli at a denser distribution of locations in the field of view are determined as a function of the tissue moduli at the sparse locations. Any now known or later developed calculation may be used.

In one embodiment, the tissue moduli or shear information, such as the shear modulus, at the non-sparse locations in the grid, is determined as a function of the strain or displacement information at the denser distribution and the moduli or shear information estimated for the sparse locations. For example, the shear modulus for each sample location is determined by iteratively solving a diffusion equation. Assuming a Poisson's ratio of 0.5 or using a known Poisson's ratio, the shear modulus at different locations is calculated iteratively as a function of the strain field at different times or under different stress for the different locations and the shear modulus for the sparse locations. Continuity in shear is assumed, so the shear modulus in different locations may be estimated from the sparse samples.

In one example embodiment, stresses at the sparse locations are calculated in act 36 as a function of the shear information from the sparse locations and as a function of the strain or displacement at the sparse locations. Knowing the strain and the shear modulus for a location, the stress may be determined. Stresses are calculated for the sparse locations as a function of the displacement information at the sparse locations and the tissue moduli at the sparse locations. In one embodiment, stresses for the sparse locations at different times are determined, such as from the strain or displacement values at different times. Stress at one time or at more than two times may be determined.

In one embodiment, densely spaced information is obtained in act 38. A simple method is to interpolate the sparse shear moduli to obtain the shear information at the dense grid. Another method is to compute the stress at sparse locations then interpolate stress at the dense grid points. The shear information at the dense grid points can be estimated from the interpolated stress values and the strain or displacement values.

In another embodiment of act 38, the diffusion of the stress is solved. Diffusion of the stress at the sparse locations is calculated for the denser sampling grid. For example, a derivative over time as a function of a second spatial derivative of the stresses at the sparse locations is determined. A diffusion equation is iteratively solved as a function of the stresses at the sparse locations to provide the stresses for the denser sampling grid. An example diffusion equation is:

$$\frac{\partial \sigma(x, y, z)}{\partial t} = \kappa(x, y, z) \nabla^2 \sigma(x, y, z),$$

subject to $$\sigma(x, y, z) = -g(r_s)\varepsilon(r_s)|_{(x,y,z)\in(r_s)}$$

where K is a diffusion constant, and σ is the stress. The diffusion constant is determined experimentally. The diffusion equation is solved iteratively. The solution is complete when the amount of change in the results is below a threshold or there is no more change. The diffusion procedure stops when the iteration approaches a predefined criterion, such as the number of iteration, the total changes of stress, or the maximum change of the stress.

The shear moduli for the different denser sampling are calculated in act 34 as a function of the diffusion. The shear moduli for each location are calculated from the strain or displacement information and the stress for each location.

Any function may be used, including functions not using the strain or displacement. One possible function is: $g(r_d) = -\sigma(r_d)/\epsilon(r_d)$ where $r_d$ is the densely sampled grid points and $\epsilon$ is the strain or displacement. The stress and strain or displacement at each of the densely distributed locations is used to determine the shear moduli at those locations. Other equations to determine the same or other tissue characteristics may be used, such as determining Young's modulus, another quantitative parameter, or a qualitative parameter.

In act 40, image data is generated as function of the calculated tissue moduli or shear information. The image data is in a display format or may be scan converted into a display format. The image data is color or gray scale data, but may be data prior to mapping with gray scale or color scale. The information is may be mapped linearly or non-linearly to the display values.

An image may be displayed from the image data. For example, the image is formed by outputting color data in a display format. The image represents the shear information or moduli (e.g., the shear moduli) for the different locations. Where the values are determined for all of the grid points in a region of interest or field of view, the pixels of the display represent the tissue characteristic for that region. The image is modulated by the shear or modulus information with the different pixels of the image corresponding to or determined from tissue property information for one or more grid points. The display grid may be different from the scan grid and/or grid for which shear or modulus information is calculated. Color, brightness, luminance, hue, or other characteristic is modulated as a function of the shear or modulus information.

More than one tissue property may be displayed in a same image. For example, pixels at one location have color responsive to one component and hue responsive to another component. The display values at different spatial locations may be responsive to different components.

The image may include other data. For example, B-mode or other data representing tissue, fluid, or contrast agents in the same region is included. The tissue property component is used for an overlay of or combination with the other data.

Figure 2:
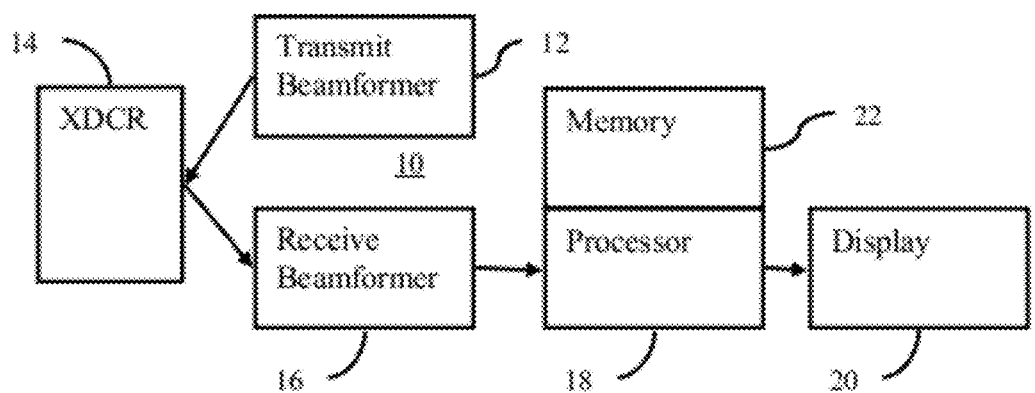
FIG. 2 is a block diagram of one embodiment of a system for determining a viscoelastic tissue property.

FIG. 2 shows one embodiment of a system 10 for determining viscoelastic tissue property. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted selection of display maps, tissue properties to be determined, region of interest selection, or other control. The system 10 is a medical diagnostic ultrasound imaging system. In alternative embodiments, the system 10 is a personal computer, workstation, PACS station, or other arrangement at a same location or distributed over a network for real-time or post acquisition imaging, so may not include the beamformers 12, 16 and transducer 14.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. A sequence of transmit beams are generated to scan a two or three-dimensional region. Sector, Vector®, linear, or other scan formats may be used. The same region is scanned multiple times. For flow or Doppler imaging and for strain imaging, a sequence of scans are used. In Doppler imaging, the sequence may include multiple beams along a same scan line before scanning an adjacent scan line. For strain imaging, scan or frame interleaving may be used (i.e., scan the entire region before scanning again). In alternative embodiments, the transmit beamformer 12 generates a plane wave or diverging wave for more rapid scanning.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for Doppler or flow data.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples.

In one embodiment, the processor 18 includes one or more detectors and a separate processor. The processor is a control processor, general processor, digital signal processor, application specific integrated circuit, field programmable gate array, network, server, group of processors, data path, combinations thereof or other now known or later developed device for determining strain, performing Fourier transforms, and calculating tissue properties. For example, the processor 18 performs any combination of one or more of the acts shown in FIG. 1.

The processor 18 applies modulus or tissue property estimation to a limited number of locations within a field of view. For example, ultrasound data is acquired for estimating shear moduli for the limited number of locations.

The processor 18 determines strain information (e.g., strain, displacement, or strain rate) as a function of the output data from the receive beamformer 16. The strain information is for a greater number of locations within the field of view than for the shear information.

The processor 18 determines viscoelastic tissue property values for the greater number of locations within the field of view than the sparse shear estimates. The tissue property values are calculated as a function of the strain information and the moduli or tissue property estimated for the limited number of locations. Any viscoelastic tissue property may be determined, such as the shear modulus. The processor 18 outputs image or display values mapped from the tissue properties to the display 20.

For determining strain information, modulus information, stress, or tissue properties, data from a plurality of scans or measurements may be acquired and stored. The data is stored in the memory 22 or a different memory. Data from one or more stages of processing is stored, such as radio frequency data, channel data, beam sum data, detected data, strain data, stress data, modulus data, shear modulus data, and/or calculated values.

The processor 18 operates pursuant to instructions stored in the memory 22 or another memory. The processor 18 is programmed for determining modulus information with ultrasound. The memory 22 is a computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 displays ultrasound images, the viscoelastic tissue property values, or other information for a plurality of spatial locations. The image represents a greater number of locations of the field of view than the number for which shear or other tissue property is determined with ultrasound.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for determining shear information with ultrasound, the method comprising:
   estimating first shear information at sparse locations of a grid;
   calculating second shear information for a more dense sampling of the grid, the more dense sampling being a sampling of a greater number of additional locations of the grid than a number of the sparse locations, the calculating of the second shear information being a function of the first shear information; and
   displaying an image as a function of the second shear information;
   wherein calculating the second shear information comprises calculating first stress at the sparse locations as a function of the first shear information, calculating diffusion of the first stress for the more dense sampling grid, and calculating the second shear information as a function of the diffusion.

2. The method of claim 1 wherein estimating the first shear information comprises estimating shear modulus.

3. The method of claim 1 wherein estimating the first shear information comprises generating a shear wave with ultrasound and measuring the shear wave with ultrasound.

4. The method of claim 1 further comprising:
   measuring strain with ultrasound at the denser sampling grid;
   wherein calculating the second shear information comprises calculating as a function of the strain.

5. The method of claim 4 wherein measuring comprises measuring the strain at different times in response to different applied stresses, the different applied stresses including the first stress.

6. The method of claim 4 wherein calculating the second shear information comprises calculating first stresses, including the first stress, for the sparse locations as a function of the first shear information and the strain, iteratively solving a diffusion equation as a function of the first stresses, the solution providing second stresses for the more dense sampling grid, and calculating the second shear information as a function of the strain and the second stresses.

7. The method of claim 1 wherein displaying the image comprises generating the image of shear modulus as a function of spatial location, different pixels of the image corresponding to the grid.

8. The method of claim 1 wherein estimating at the sparse locations of the grid comprises estimating at a subset of grid points, and wherein calculating for the more dense sampling comprises calculating for a set of the grid points, the grid points of the subset being regularly spaced at a ratio of 1/5 or less of the grid points of the subset to the grid points of the set.

9. The method of claim 1 wherein estimating at the sparse locations comprises estimating for the sparse locations in a two-dimensional area having at least five scan lines, and wherein calculating for the more dense sampling comprises calculating for grid points in the two-dimensional area and on the at least five scan lines.

10. In a non-transitory computer readable storage medium having stored therein data representing instructions executable by a programmed processor for determining modulus information with ultrasound, the storage medium comprising instructions for:
    estimating, with ultrasound response, tissue moduli at sparse locations in a field of view;
    measuring, with ultrasound, displacement information in response to a force applied to tissue; and
    determining, as a function of the tissue moduli at the sparse locations, tissue moduli at dense locations in the field of view, wherein determining comprises calculating the tissue moduli at the dense locations using the displacement information and the tissue moduli at the sparse locations.

11. The non-transitory computer readable medium of claim 10 wherein determining comprises determining the tissue moduli at fully sampled locations in the field of view.

12. The non-transitory computer readable medium of claim 10 further comprising:
generating image data as a function of the tissue moduli.

13. In a non-transitory computer readable storage medium having stored therein data representing instructions executable by a programmed processor for determining modulus information with ultrasound, the storage medium comprising instructions for:
estimating, with ultrasound response, tissue moduli at sparse locations in a field of view;
determining, as a function of the tissue moduli at the sparse locations, tissue moduli at dense locations in the field of view; and
measuring, with ultrasound, displacement information in response to a force applied to tissue;
wherein determining comprises calculating stresses for the sparse locations as a function of the displacement information at the sparse locations and the tissue moduli at the sparse locations, calculating stresses for the dense locations as a function of the stresses at the sparse locations, and determining shear moduli as a function of the stresses at the dense locations and the displacements at the dense locations.

14. The non-transitory computer readable medium of claim 13 wherein calculating stresses for the dense locations comprises determining a derivative over time as a function of a second spatial derivative of the stresses at the sparse locations.

15. A system for determining viscoelastic tissue property, the system comprising:
a transducer configured to generate receive signals from received ultrasound energy;
a receive beamformer configured to output data representing spatial locations along at least a line;
a processor configured to apply modulus estimation to a limited number of locations within a field of view, generate strain information as a function of the output data, the strain information being for a greater number of locations within the field of view, and calculate viscoelastic tissue property values for the greater number of locations within the field of view using the strain information and the moduli estimated for the limited number of locations.

16. The system of claim 15 further comprising:
a display configured to display the viscoelastic tissue property values for a plurality of spatial locations representing the greater number of locations of the field of view.

17. The system of claim 15 wherein the processor is configured to estimate shear moduli for the limited number of locations and operable to determine shear moduli as the viscoelastic tissue property.

* * * * *